United States Patent
Taylor

(10) Patent No.: US 8,128,671 B2
(45) Date of Patent: Mar. 6, 2012

(54) VARIABLE FLANK BONE SCREW

(75) Inventor: Harold Taylor, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 653 days.

(21) Appl. No.: 11/732,741

(22) Filed: Apr. 4, 2007

(65) Prior Publication Data

US 2008/0249579 A1  Oct. 9, 2008

(51) Int. Cl.
*A61B 17/04* (2006.01)
*A61B 17/86* (2006.01)
*A61F 2/08* (2006.01)
*F16B 39/30* (2006.01)
*F16B 35/04* (2006.01)

(52) U.S. Cl. .................. 606/315; 411/308; 411/415

(58) Field of Classification Search .................. 606/300, 606/309, 315–317; 411/265, 267, 283, 307, 411/308, 310, 311, 411, 412, 414, 423, 426; 408/233
See application file for complete search history.

(56) References Cited

U.S. PATENT DOCUMENTS

| | | | | |
|---|---|---|---|---|
| 3,520,344 A | * | 7/1970 | Gabbey | 411/308 |
| 3,664,400 A | * | 5/1972 | Moore | 411/308 |
| 3,861,269 A | | 1/1975 | Laverty | |
| 4,150,702 A | * | 4/1979 | Holmes | 411/310 |
| 4,572,875 A | * | 2/1986 | Gutshall | 428/585 |
| 4,844,676 A | * | 7/1989 | Adamek | 411/386 |
| 5,120,171 A | | 6/1992 | Lasner | |
| 5,242,447 A | | 9/1993 | Borzone | |
| 5,259,398 A | * | 11/1993 | Vrespa | 128/898 |
| 5,385,439 A | * | 1/1995 | Hurdle | 411/386 |
| 5,395,371 A | | 3/1995 | Miller et al. | |
| 5,409,486 A | | 4/1995 | Reese | |
| 5,456,685 A | | 10/1995 | Huebner | |
| 5,492,442 A | | 2/1996 | Lasner | |
| 5,520,688 A | | 5/1996 | Lin | |
| 5,540,690 A | | 7/1996 | Miller et al. | |
| 5,545,163 A | | 8/1996 | Miller et al. | |
| 5,601,553 A | | 2/1997 | Trebing et al. | |
| 5,607,428 A | | 3/1997 | Lin | |
| 5,613,968 A | | 3/1997 | Lin | |
| 5,643,263 A | | 7/1997 | Simonson | |
| 5,738,685 A | | 4/1998 | Halm et al. | |
| 5,779,417 A | | 7/1998 | Barth et al. | |
| 5,814,046 A | | 9/1998 | Hopf | |
| 5,947,967 A | | 9/1999 | Barker | |
| 6,045,312 A | | 4/2000 | Hsing | |
| D427,684 S | * | 7/2000 | Hansson | D24/156 |
| 6,086,303 A | * | 7/2000 | Fluckiger | 411/399 |
| 6,116,832 A | * | 9/2000 | Wolf et al. | 411/383 |
| 6,129,730 A | | 10/2000 | Bono et al. | |

(Continued)

FOREIGN PATENT DOCUMENTS

GB    2198801 A  *  6/1988

(Continued)

*Primary Examiner* — Thomas C. Barrett
*Assistant Examiner* — David Bates

(57) ABSTRACT

A bone screw comprising a threaded shank having a longitudinal axis and including a first helical threading extending along a first length of the threaded shank portion and a second helical threading extending from a location proximately adjacent the first helical threading and along a second length of the threaded shank portion. The first helical threading defines a first volume between adjacent thread turns along the first length, and the second helical threading defines a second volume between adjacent thread turns along the second length, with the first volume being different from the second volume.

29 Claims, 5 Drawing Sheets

U.S. PATENT DOCUMENTS

| | | | |
|---|---|---|---|
| 6,224,602 B1 | 5/2001 | Hayes | |
| 6,368,319 B1 | 4/2002 | Schaefer | |
| 6,471,703 B1 | 10/2002 | Ashman | |
| 6,508,820 B2* | 1/2003 | Bales | 606/62 |
| 6,585,740 B2 | 7/2003 | Schlapfer et al. | |
| 6,602,256 B1 | 8/2003 | Hayes | |
| 7,264,470 B2* | 9/2007 | Hansson | 433/174 |
| 7,559,846 B2* | 7/2009 | Ferrell | 470/66 |
| 2002/0016594 A1 | 2/2002 | Schlapfer et al. | |
| 2003/0026675 A1* | 2/2003 | McGovern et al. | 411/412 |
| 2003/0153911 A1* | 8/2003 | Shluzas | 606/61 |
| 2004/0141827 A1* | 7/2004 | Dicke | 411/413 |
| 2004/0172031 A1 | 9/2004 | Rubecamp et al. | |
| 2004/0210227 A1 | 10/2004 | Trail et al. | |
| 2007/0233122 A1* | 10/2007 | Denis et al. | 606/73 |
| 2009/0062868 A1* | 3/2009 | Casutt | 606/316 |

FOREIGN PATENT DOCUMENTS

| | | |
|---|---|---|
| WO | WO 94/01048 | 1/1994 |

\* cited by examiner

VARIABLE FLANK BONE SCREW

FIELD OF THE INVENTION

The present invention relates generally to the field of bone screws, and more particularly relates to a bone screw having variable flank characteristics.

BACKGROUND

Various types of fasteners are used to engage implants and other devices to bone. In the spinal field, bone screws are commonly used to attach plates, rods and other types of implants and devices to one or more vertebrae. Many existing bone screws include a threaded shank portion adapted for engagement in bone, and a head portion for coupling to an elongate member such as a spinal rod via a connector mechanism. The threaded shank portion of the bone screw typically includes a single, constant pitch threading having a constant and uniform flank and flank angle suitable for engagement or purchase of cancellous bone. However, conventional bone screw threadings are not particularly suitable for engagement or purchase of different types or regions of bone, such as the cancellous and cortical regions of bone, and also do not lend to providing increased support and stability to the bone screw when driven into bone.

There remains a need for an improved bone screw. The present invention satisfies this need and provides other benefits and advantages in a novel and unobvious manner.

SUMMARY

The present invention relates generally to the field of bone screws, and more particularly relates to a bone screw having variable flank characteristics. While the actual nature of the invention covered herein can only be determined with reference to the claims appended hereto, certain forms of the invention that are characteristic of the preferred embodiments disclosed herein are described briefly as follows.

In one form of the present invention, a bone screw is provided including a threaded shank having a longitudinal axis and including a first helical threading extending along a first length of the threaded shank portion and a second helical threading extending from a location proximately adjacent the first helical threading and along a second length of the threaded shank portion, with the first helical threading defining a first substantially constant volume between adjacent thread turns along the first length, and the second helical threading defining a second substantially constant volume between adjacent thread turns along the second length, and wherein the first volume is different from the second volume.

In another form of the present invention, a bone screw is provided including a threaded shank portion having a longitudinal axis and including a first helical threading extending along a first length of the threaded shank portion and a second helical threading extending from a location proximately adjacent the first helical threading and along a second length of the threaded shank portion, with the first helical threading defining a first substantially constant thread crest width along the first length, and the second helical threading defining a second substantially constant thread crest width along the second length, and wherein the first thread crest width is different from the second thread crest width.

In a further form of the present invention, a bone screw is provided including a threaded shank portion having a longitudinal axis and defining a substantially constant thread root diameter, a substantially constant thread outer diameter, and a substantially constant thread pitch, with the threaded shank portion including a first helical threading extending along a first length of the threaded shank portion and a second helical threading extending from a location proximately adjacent the first helical threading and along a second length of the threaded shank portion, and with the first helical threading defining a first volume between adjacent thread turns and the second helical threading defining a second volume between adjacent thread turns, and wherein the first volume is different from the second volume.

In still another form of the present invention, a bone screw is provided including a threaded shank having a longitudinal axis and including a first helical threading extending along a first length of the threaded shank portion and a second helical threading extending from a location proximately adjacent the first helical threading and along a second length of the threaded shank portion, with the first helical threading defining a first volume between adjacent thread turns, and the second helical threading defining a second volume between adjacent thread turns, and wherein said first volume is different from the second volume. Additionally, the first helical threading transitions into the second helical threading at a transition region wherein a portion of the second helical threading overlaps an axially adjacent portion of the first helical threading and extends from a location adjacent a thread root diameter and gradually increases to an outer thread diameter.

It is one object of the present invention to provide an improved bone screw. Further objects, features, advantages, benefits, and aspects of the present invention will become apparent from the drawings and description contained herein.

DESCRIPTION

Figure 1:
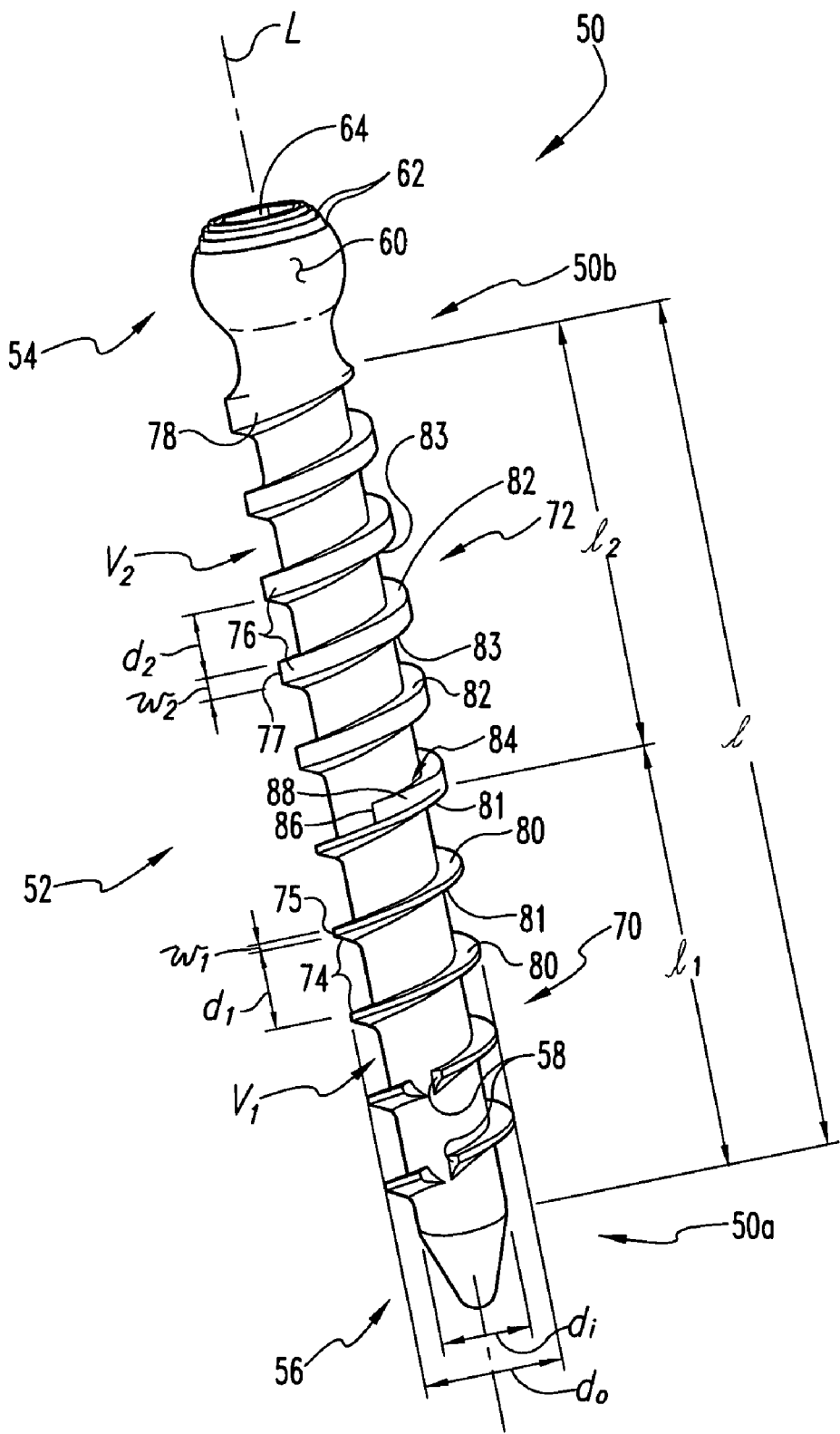
FIG. 1 is an elevational perspective view of a bone screw according to one form of the present invention.

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Referring to FIG. 1, shown therein is a bone screw 50 according to one form of the present invention. The bone screw 50 extends along a longitudinal axis L and includes a distal end portion 50a and a proximal end portion 50b. The bone screw 50 generally includes a threaded shank portion 52 adapted for engagement within bone, and a head portion 54 adapted for coupling with an implant, further details of which will be set forth below. The bone screw 50 may be formed of any suitable biocompatible material such as, for example, titanium, a titanium alloy, stainless steel, metallic alloys, or other materials known to those of skill in the art that possess the mechanical and biocompatible properties suitable for implantation within the body and anchoring to bone.

In one embodiment, the threaded shank 52 includes a distal tip 56 that is configured to penetrate bone. In the illustrated embodiment, the distal tip 56 is tapered to facilitate entry into bone. However, in other embodiments, the distal tip 56 may define a blunt or rounded end. Additionally, in the illustrated embodiment, the distal end portion 50a is provided with one or more cutting edges 58 to provide the bone screw 50 with self-cutting or self-tapping capabilities. The cutting edges 58 are formed by a cutting flute extending axially across the first two thread turns. However, it should be understood that the cutting flute may extend over a single thread turn or may extend over three or more thread turns. In other embodiments, the bone screw 50 may be provided with an axial passage (not shown) extending from the proximal end portion 50b and partially or entirely therethrough to define a cannulation opening, and may be further provided with transverse passages that communicate with the axial passage to define fenestration openings. The cannulation and fenestration openings may be used to deliver material such as, for example, bone cement from the proximal end portion 50b of the bone screw 50 and into areas of the bone axially or laterally adjacent the distal end portion 50a or other portions of the threaded shank 52.

In the illustrated embodiment, the head portion 54 comprises a spherical-shaped head portion defining a substantially spherical-shaped outer surface 60. The spherical-shaped head portion 54 further defines a number of annular grooves or ridges 62 formed along the proximal portion of the head portion 54 to facilitate locking engagement of the spherical shaped head portion 54 with an intermediate member such as, for example, a crown member or other types and configurations or locking members that would occur to one of skill in the art, such that the bone screw 50 may be locked at a select angular orientation relative to the coupling element. The bone screw 50, and particularly the screw head portion 54, preferably includes features that allow for releasable engagement with a driving tool or instrument (not shown) such as, for example, a screwdriver. In the illustrated embodiment, the screw head portion 54 defines a tool-receiving cavity or recess 64 sized and shaped to receive a distal end portion of a driver tool. The cavity or recess is preferably non-circular such as, for example, hexagonal shaped to provide non-rotational engagement between the head portion 54 and the driver tool to facilitate driving engagement of the bone screw 50 into bone. Alternatively, the screw head portion 54 may define external surface features for engagement by the distal end portion of a driver tool. Although the bone screw 50 is illustrated and described as having a particular type and configuration of a screw head portion, it should be understood that other types and configuration of screw head portions are also contemplated, several examples of which will be discussed below.

Figure 2:
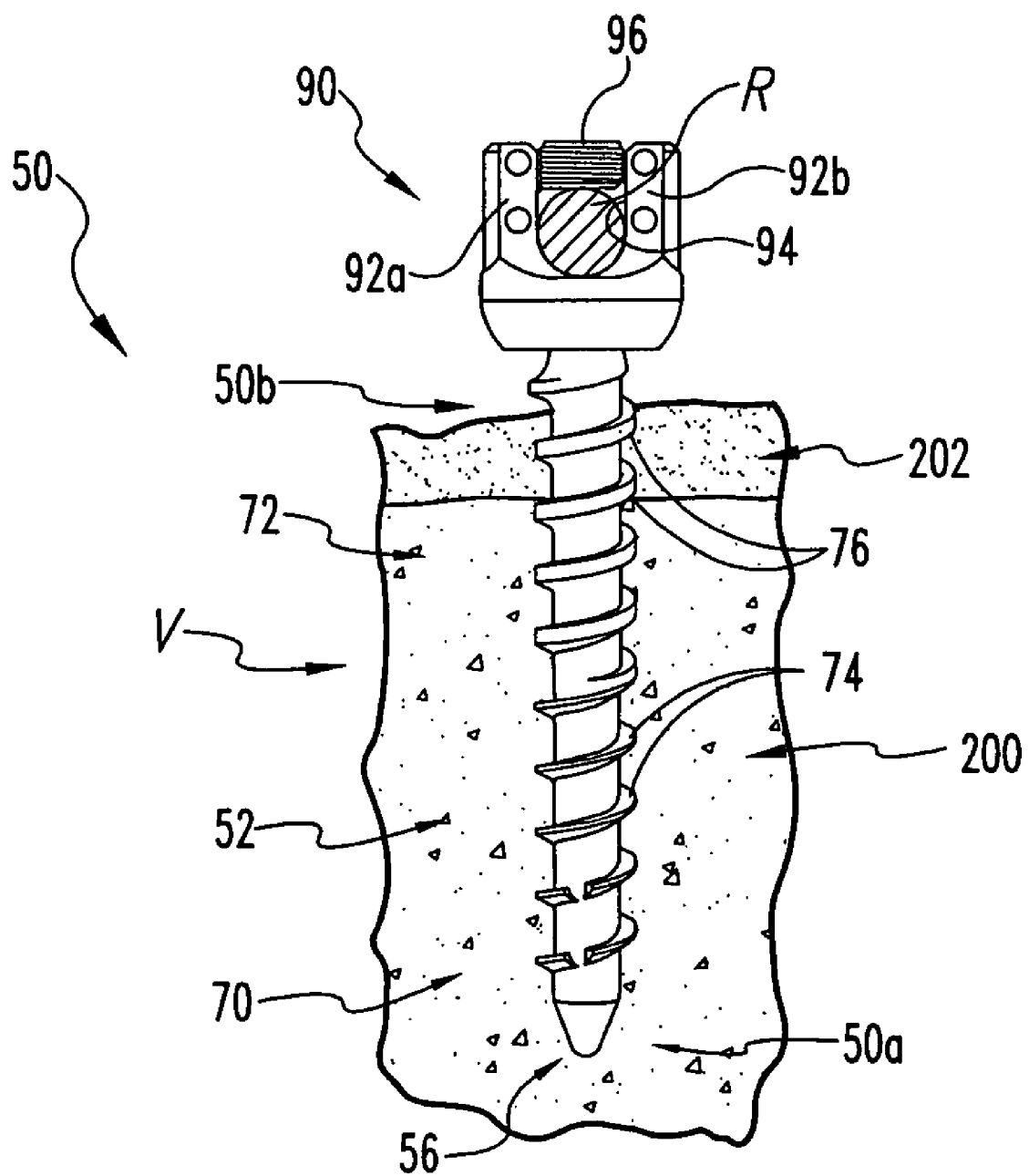
FIG. 2 is an elevational side view of the bone screw illustrated in FIG. 1, as engaged to bone and as coupled to a spinal rod.

Referring to FIG. 2, the spherical-shaped head portion 54 of the bone screw 50 is configured to be rotatably received within a spherical-shaped passage formed in a coupling element or receiver member 90 to allow the bone screw 50 to be pivoted relative to the coupling element 90 about a single axis or about multiple axes. The coupling element 90 includes axially extending arms 92a, 92b which define a U-shaped channel 94 sized and configured to receive a spinal rod R or other types of spinal implants that would occur to one of skill in the art. The spinal rod R is captured within the channel 94 via a fastener or set screw 96 engaged between the arms 92a, 92b of the coupling element 90. Further details regarding the coupling element 90 and engagement of the coupling element 90 and the head portion 54 of the bone screw 50 are known to those of skill in the art and need not be discussed herein. Various types and configurations of bone screws having spherical-shaped head portions and coupling elements or receiver members configured for rotatable engagement with the spherical-shaped head portions are illustrated and described, for example, in U.S. Pat. No. 5,728,098 to Sherman et al., U.S. Pat. No. 6,053,917 to Sherman et al. and U.S. Pat. No. 6,660,004 to Barker et al., the contents of each patent reference hereby incorporated by reference in its entirety.

Referring once again to FIG. 1, the threaded shank 52 has an overall length l and defines a first threaded section 70 extending along a first shank length $l_1$ from the distal end portion 50a toward the proximal end portion 50b, and a second threaded section 72 extending contiguously from the first threaded section 70 toward the proximal end portion 50b along a second shank length $l_2$. As will be discussed in greater detail below, the first threaded section 70 includes a first helical threading 74 for anchoring in a cancellous region of bone, and the second threaded section 72 includes a second helical threading 76 for anchoring in a cortical region of bone and in cancellous bone adjacent the cortical region. Additionally, the second threaded section 72 may be provided with a thread run out 78 adjacent the proximal end portion 50b of the threaded shank 52 near the head portion 54.

In one embodiment, the length $l_1$ of the first threaded section 70 extends along about one half of the overall length l of the threaded shank 52, with the length $l_2$ of the second threaded section 72 extending along the remainder of the overall shank length l. In another embodiment, the length $l_1$ of the first threaded section 70 extends along more than one half of the overall shank length $l_1$ with the length $l_2$ of the second threaded section 72 extending along less than one half of the overall shank length l. In a further embodiment, the length $l_1$ of the first threaded section 70 extends along at least about two-thirds of the overall shank length l, with the length $l_2$ of the second threaded section 72 extending along the remainder of the overall shank length l. In still another embodiment, the length $l_1$ of the first threaded section 70 extends along at least about three-quarters of the overall shank length l, with the length $l_2$ of the second threaded section 72 extending along the remainder of the overall shank length l. However, it should be understood that other lengths $l_1$, $l_2$ of the first and second threaded sections 70, 72 are also contemplated as falling within the scope of the present invention. The particular ratio between the lengths $l_1$ and $l_2$ associated with the first and second threaded sections 70, 72 may be selected based on the particular characteristics of the bone to which the bone screw 50 is to be engaged.

In the illustrated embodiment of the invention, the first and second helical threadings 74, 76 cooperate with one another to define a single thread lead defining a helical thread pattern extending substantially continuously along virtually the entire overall length l of the shank portion 52. However, in other embodiments, at least a portion of the first and second helical threadings 74, 76 may be interleaved with one another to define a dual lead thread extending along at least a portion of the overall shank length l. One embodiment of a bone screw having a dual lead thread is illustrated and described in U.S. patent application Ser. No. 11/355,877 filed on Feb. 16, 2006, the contents of which are incorporated herein by reference in their entirety. Additionally, in the illustrated embodiment of the invention, the first and second helical threadings 74, 76 define a substantially constant and uniform thread pitch along the shank length l, and a substantially constant and uniform outer thread diameter $d_o$ and thread root diameter $d_i$ along the shank length l. However, in other embodiments, the first and second helical threadings 74, 76 may define a variable thread pitch along at least a portion of the shank length l, and/or may define a tapering outer thread diameter $d_o$ and/or a tapering thread root diameter $d_i$ extending along at least a portion of the shank length l.

In the illustrated embodiment of the invention, the first helical threading 74 includes a thread crest 75 having a crest width $w_1$, and upper and lower thread flanks 80 and 81 extending from the thread crest 75 to the thread root diameter $d_i$, with the upper and lower flanks 80, 81 each arranged at substantially equal flank angles. Similarly, the second helical threading 76 includes a thread crest 77 having a crest width $w_2$, and upper and lower thread flanks 82 and 83 extending from the thread crest 77 to the thread root diameter $d_i$, with the upper and lower flanks 82, 83 each arranged at substantially equal flank angles. In the illustrated embodiment, the thread crests 75, 77 are substantially flat or planar and extend generally parallel with the longitudinal axis L. However, other embodiments are also contemplated wherein the thread crest 75 and/or the thread crest 77 may be rounded, angled or pointed, or may be provided with other thread crest configurations that would occur to one of skill in the art.

In one embodiment of the invention, the upper and lower flanks 80, 81 of the first helical threading 74 are generally symmetrical relative to the thread crest 75, and the upper and lower flanks 82, 83 of the second helical threading 76 are generally symmetrical relative to the thread crest 77. The flank angle of a symmetrical thread is commonly referred to by those of skill in the art as the half-angle of the thread. However, it should be understood that the upper and lower flanks 80, 81 of the first helical threading 74 and/or the upper and lower flanks 82, 83 of the second helical threading 76 need not necessarily be symmetrical. Instead, the upper flank 80 of the first helical threading 74 may be arranged at a flank angle that is different from the flank angle of the lower flank 81, and/or the upper flank 82 of the second helical threading 76 may be arranged at a flank angle that is different from the flank angle of the lower flank 83. Additionally, in the illustrated embodiment of the invention, the half-angle of the first helical threading 74 is substantially equal to the half-angle of the second helical threading 76. However, it should be understood that in other embodiments, the half-angles of the first and second helical threadings 74, 76 need not necessarily be equal to or even substantially equal to one another.

As indicated above, the thread crest 75 of the first helical threading 74 has a crest width $w_1$, thereby defining a distance $d_1$ between the upper and lower flanks 80, 81 of adjacent turns of the first helical threading 74. Similarly, the thread crest 77 of the second helical threading 76 has a crest width $w_2$, thereby defining a distance $d_2$ between the upper and lower flanks 82, 83 of adjacent turns of the second helical threading 76. In the illustrated embodiment of the invention, the crest width $w_1$ of the first helical threading 74 substantially differs from that of the crest width $w_2$ of the second helical threading 76. In one embodiment of the invention, the crest width $w_1$ is approximately one-half that of the crest width $w_2$. In another embodiment of the invention, the crest width $w_1$ is approximately one-third that of the crest width $w_2$. In a further embodiment of the invention, the crest width $w_1$ is approximately two-third that of the crest width $w_2$. However, it should be understood that other ratios between the crest width $w_1$ and the crest width $w_2$ are also contemplated as falling within the scope of the present invention.

As should be appreciated, providing the first and second helical threadings 74, 76 with different crest widths $w_1$, $w_2$ correspondingly defines different distances $d_1$ and $d_2$ between the upper and lower flanks of adjacent thread turns of the first and second helical threadings 74, 76. As a result, the volume $v_1$ between adjacent thread turns of the first helical threading 74 (between the opposing upper and lower flanks 80, 81) differs from the volume $v_2$ between adjacent thread turns of the second helical threading 76 (between the opposing upper and lower flanks 82, 83). Stated another way, the cross sectional area defined between adjacent thread turns of the first helical threading 74 differs from the cross sectional area defined between adjacent thread turns of the second helical threading 76. As should be appreciated, in embodiments of the invention where the crest width $w_2$ of the second helical threading 76 is greater than the crest width $w_1$ of the first helical threading 74, the distance $d_2$ and volume $v_2$ between the opposing upper and lower flanks 82, 83 of the second helical threading 76 is less than the distance $d_1$ and volume $v_1$ between the opposing upper and lower flanks 80, 82 of the first helical threading 74. In one embodiment of the invention, the distance $d_2$ and volume $v_2$ between the opposing upper and lower flanks 82, 83 of the second helical threading 76 is at least about five percent less than the distance $d_1$ and volume $v_1$ between the opposing upper and lower flanks 80, 82 of the first helical threading 74. In another embodiment, the distance $d_2$ and volume $v_2$ between the opposing upper and lower flanks 82, 83 of the second helical threading 76 is at least about ten percent less than the distance $d_1$ and volume $v_1$ between the opposing upper and lower flanks 80, 82 of the first helical threading 74. However, it should be understood that other embodiments are also contemplated including different ratios between the distance $d_2$/volume $v_2$ and the distance $d_1$/volume $v_1$.

In the illustrated embodiment of the invention, the first helical threading 74 transitions into the second helical threading 76 at a transition region 84. The transition region 84 is formed via the disposition of a portion of the second helical threading 76 proximately adjacent a corresponding portion of the first helical threading 74 in an axially-overlapping or interleaved configuration. The axially-overlapping portions of the first and second helical threadings 74, 76 are preferably contiguous with one another so as to define a unitary and substantially uninterrupted threading. In one embodiment, the transition region 84 is formed via a portion of the second helical threading 76 extending from a location adjacent the thread root diameter $d_i$, gradually increasing in diameter to the outer thread diameter $d_o$ and eventually transitioning into the thread crest 77 of the second helical threading 76. In a further embodiment, a portion of the second helical threading 76 extends from an edge or transition location 86 adjacent the thread root diameter $d_i$ and defines an outwardly tapering thread surface 88, gradually increasing in diameter and eventually transitioning to the outer diameter of the thread crest 75 of the first helical threading 74, thereby forming the thread crest 77 of the second helical threading 76. In this manner, the first and second helical threadings 74, 76 are generally contiguous with one another so as to define a unitary and substantially uninterrupted threading which is devoid of any abrupt transitions or sharp edges or projections that might otherwise shear or break off bone material as the threaded shank 52 of the bone screw 50 is driven into bone.

In one form of the invention, the first and second helical threadings 74, 76 and the transition region 84 are provided by initially forming the second helical threading 76 along the overall length l of the threaded shank 52, and by subsequently removing or cutting away a portion of the second helical threading 76 along the length $l_1$ of the first threaded section 70 to thereby provide the first helical threading 74 with a reduced thread crest width $w_1$ relative to the thread crest width $w_2$ of the second helical threading 76. As should be appreciated, a portion of the second helical threading 76 is gradually removed or cut away adjacent the transition region 84 so as to provide the outwardly tapering thread surface 88 extending from the transition location 86 adjacent the thread root diameter $d_i$ to the outer thread diameter $d_o$ defined by the thread crest 77 of the second helical threading 76. However, it should be understood that other methods and techniques of forming the first and second helical threadings 74, 76 and/or the transition region 84 are also contemplated as falling within the scope of the present invention.

In one embodiment of the invention, the distance $d_1$ and volume $v_1$ between adjacent thread turns of the first helical threading 74 is relatively constant and uniform along substantially the entire length $l_1$ of the first threaded section 70. Similarly, the distance $d_2$ and volume $v_2$ between adjacent thread turns of the second helical threading 76 is relatively constant and uniform along substantially the entire length $l_2$ of the second threaded section 72. However, it should be understood that in other embodiments of the invention, the distance $d_1$ and volume $v_1$ between adjacent thread turns of the first helical threading 74 may gradually vary along at least a portion of the length $l_1$ of the first threaded section 70 to provide a uniformly varying configuration defining a constant and continual increase in the distance $d_1$ and volume $v_1$, or may abruptly vary along at least a portion of the length $l_1$ of the first threaded section 70 to provide a stair-step configuration defining an incremental increase in the distance $d_1$ and volume $v_1$. Similarly, the distance $d_2$ and volume $v_2$ between adjacent thread turns of the second helical threading 76 may gradually vary along at least a portion of the length $l_2$ of the second threaded section 72 to provide a uniformly varying configuration defining a constant and continual increase in the distance $d_2$ and volume $v_2$, or may abruptly vary along at least a portion of the length $l_2$ of the second threaded section 72 to provide a stair-step configuration defining an incremental increase in the distance $d_2$ and volume $v_2$.

As will be further discussed below, when the bone screw 50 is threaded into bone, the first threaded section 70 will engage the bone and bone material will be directed into the volume $v_1$ between adjacent upper and lower flanks 80, 81 of the first helical threading 74. Additionally, as the bone screw 50 is further threaded into the bone, the second threaded section 72 will engage the bone with the bone material directed into the volume $v_2$ between adjacent upper and lower flanks 82, 83 of the second helical threading 76. Since the volume $v_2$ between the adjacent upper and lower flanks 82, 83 of the second helical threading 76 is reduced compared to the volume $v_1$ between the adjacent upper and lower flanks 80, 81 of the first helical threading 74, the bone material directed into the volume $v_2$ will be compressed or compacted between the upper and lower flanks 82, 83 as the second threaded section 72 is driven into the bone. Compression or compaction of bone material between the upper and lower flanks 82, 83 of the second helical threading 76 tightens the bone screw 50 within the bone, thereby tending to provided more secure and stable anchoring of the bone screw 50 within the bone. The denser and more compact thread configuration of the second helical threading 76 also tends to provide more secure and stable anchoring of the bone screw 50 within the relatively harder and denser cortical region of bone. However, it should be understood that the first and second helical threadings 74, 76 may be anchored within any type of bone, including the same type of bone.

In the illustrated embodiment of the invention, the distance $d_2$ and volume $v_2$ between adjacent thread turns of the second helical threading 76 is reduced relative to the distance $d_1$ and volume $v_1$ between adjacent thread turns of the first helical threading 74 via an increase in the width $w_2$ of the thread crest 77 relative to the width $w_1$ of the thread crest 75, with the flank angles associated with the first and second helical threadings 74, 76 remaining substantially constant and substantially equal to one another. However, it should be understood that the volume $v_2$ between adjacent thread turns of the second helical threading 76 may be reduced relative to the volume $v_1$ between adjacent thread turns of the first helical threading 74 by varying the flank angles associated with the first helical threading 74 relative to flank angles associated with the second helical threading 76. For example, increasing the half-angle of the second helical threading 76 relative to the half-angle of the first helical threading 74 will correspondingly reduce the volume $v_2$ relative to the volume $v_1$. Additionally, in other embodiments, the volume $v_2$ may be reduced relative to the volume $v_1$ by varying other characteristics associated with the thread flanks such as, for example, by varying the shape of the upper flank 80 and/or the lower flank 81 associated with the first helical threading 74 relative to the upper flank 82 and/or the lower flank 83 associated with the second helical threading (e.g. smooth/flat flanks vs. curved/arcuate flanks, varying the curvature of the flanks, etc.). Additionally, it should be understood that the volume $v_2$ may be further varied relative to the volume $v_1$ by varying the thread root diameter $d_i$ of the first helical threading 74 relative to the second helical threading 76, by varying the height of the first helical threading 74 relative to the second helical threading 76, and/or by varying the pitch of the first helical threading 74 relative to the second helical threading 76.

Figure 3:
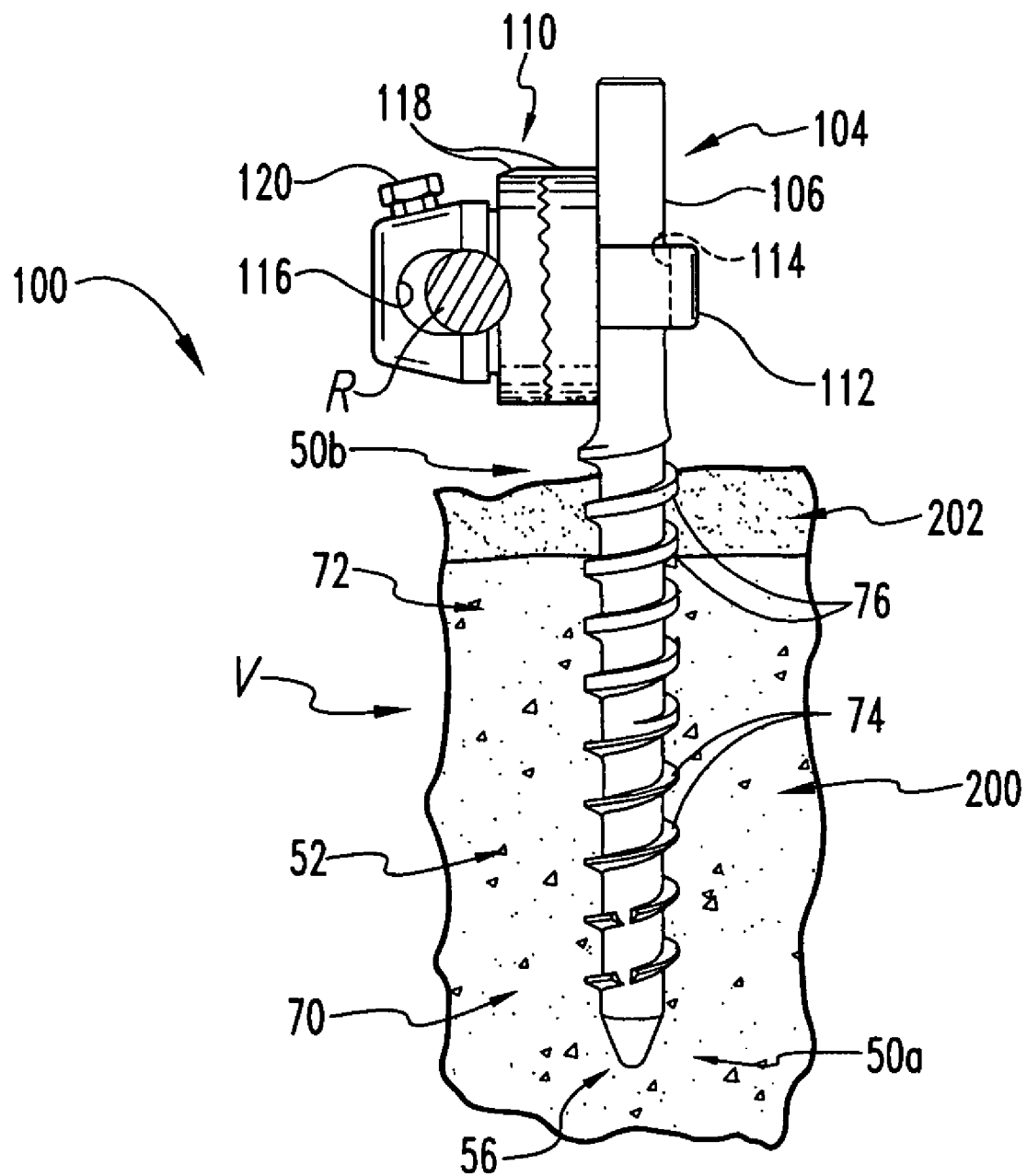
FIG. 3 is an elevational side view of a bone screw according to another form of the present invention, as engaged to bone and as coupled to a spinal rod.

Referring to FIG. 3, shown therein is a bone screw 100 according to another form of the invention. Specifically, the bone screw 100 includes a threaded shank 52 and a head portion 104 that is adapted for coupling with a spinal implant. The threaded shank 52 is identical to that described above and illustrated in FIGS. 1 and 2. In the illustrated embodiment, the screw head portion 104 comprises an unthreaded stem portion or shaft 106, and the implant comprises an elongate spinal rod R that is coupled to the screw head 104 via a connector mechanism 110. The connector mechanism 110 includes a connector body 112 defining a first passage 114 for receiving the stem portion 106 of the screw head 104, and a second passage 116 for receiving the spinal rod R. An interface member 118 may be positioned between the spinal rod R and the stem portion 106, and a fastener or set screw 120 is threaded through an opening in the connector body 112 and into contact with the spinal rod R, which in turn engages the interface member 118 with the stem portion 106 of the screw head 104 to fix the angular relationship between the spinal rod R and the bone screw 100. Further details regarding the connector mechanism 110 and other types of connector mechanisms are illustrated and described, for example, in U.S. Pat. No. 5,643,263 to Simonson, U.S. Pat. No. 5,947,967 to Barker and U.S. Pat. No. 6,471,703 to Ashman, the contents of each patent reference hereby incorporated by reference in its entirety.

Figure 4:
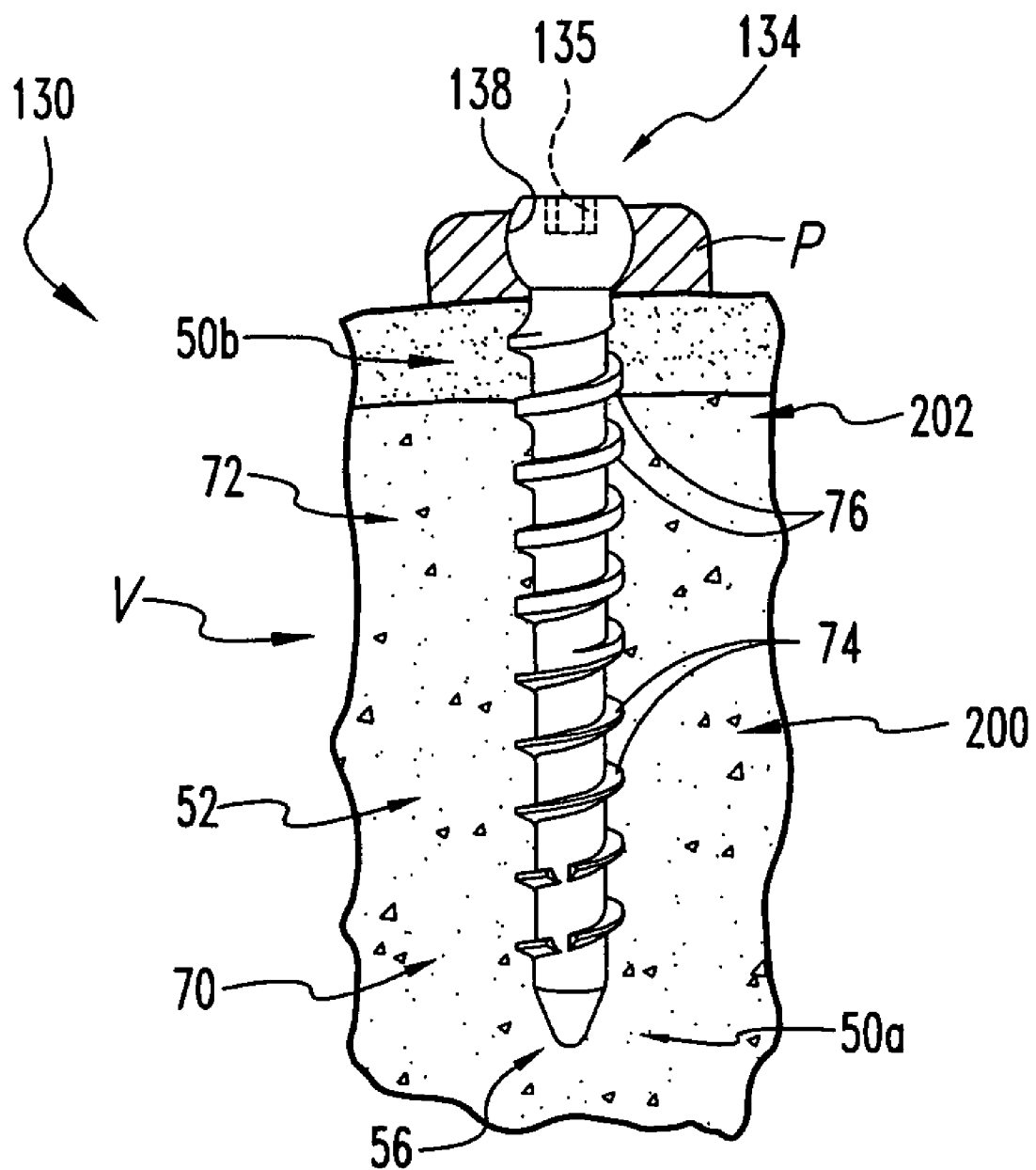
FIG. 4 is an elevational side view of a bone screw according to another form of the present invention, as engaged to bone and as coupled to a spinal plate.

Referring to FIG. 4, shown therein is a bone screw 130 according to another form of the invention. Specifically, the bone screw 130 includes a threaded shank 52 and a head portion 134 that is adapted for coupling with a spinal implant. The threaded shank 52 is identical to that described above and illustrated in FIGS. 1 and 2. In the illustrated embodiment, the screw head portion 134 comprises a spherical-shaped head configured similar to the spherical-shaped head portion 54 illustrated and described above with regard to the bone screw 50, including a tool-receiving cavity or recess 135. However, the spherical-shaped head 54 is adapted to engage an elongate spinal plate P. The spinal plate P includes one or more openings 136 for receiving one or more of the bone screws 130. In the illustrated embodiment, the openings 136 include a lower portion sized to receive the threaded shank 52 therethrough, and an upper spherical-shaped portion 138 sized to receive the spherical-shaped head portion 134 of the bone screw 130. As should be appreciated, threading of the bone screw 130 into the bone compresses the spinal plate P against an outer surface of the bone, thereby capturing the spinal plate P between the spherical-shaped head portion 134 and the outer surface of the bone.

Figure 5:
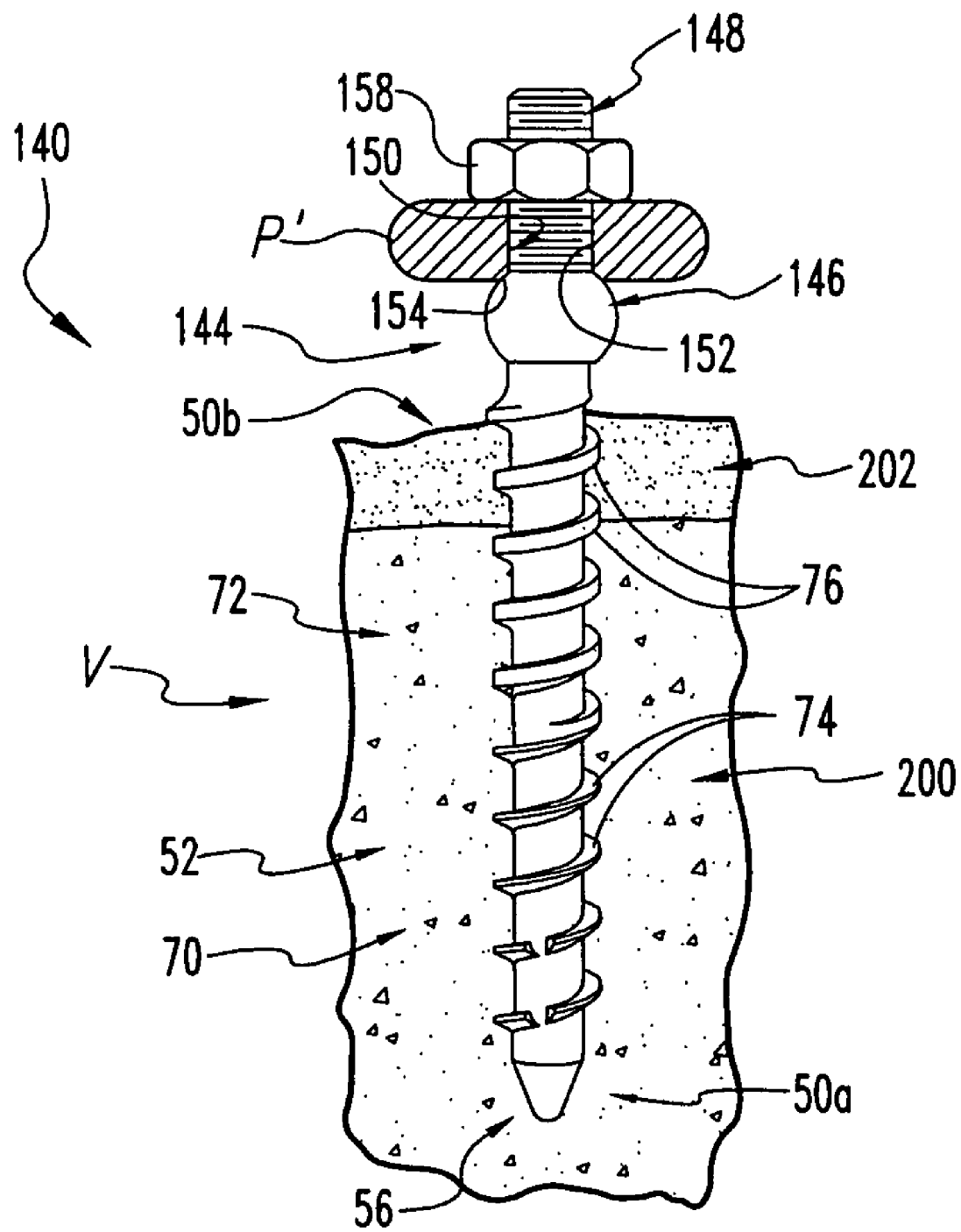
FIG. 5 is an elevational side view of a bone screw according to another form of the present invention, as engaged to bone and as coupled to a spinal plate.

Referring to FIG. 5, shown therein is a bone screw 140 according to another form of the invention. Specifically, the bone screw 140 includes a threaded shank 52 and a head portion 144 that is adapted for coupling with a spinal implant. The threaded shank 52 is identical to that described above and illustrated in FIGS. 1 and 2. In the illustrated embodiment, the screw head portion 144 is adapted to engage an elongate spinal plate P and includes a spherical-shaped head portion 146 and a threaded stem portion 148 extending from the spherical-shaped head portion 146. The spinal plate P' includes one or more openings 150 for receiving one or more of the bone screws 140. In the illustrated embodiment, the openings 150 include an upper portion 152 through which extends the threaded stem portion 148, and a lower spherical-shaped portion 154 sized to receive the spherical-shaped head portion 146. As should be appreciated, the spinal plate P' is secured to the bone screw 140 via a lock nut 158 which is threaded onto the threaded stem portion 148, thereby capturing the spinal plate P' between the spherical-shaped head portion 146 and the lock nut 158. As should be appreciated, the bone screw 140 illustrated in FIG. 5 allows the spinal plate P' to be spaced from the outer surface of the bone.

Having described the components and features associated with the present invention, reference will now be made to a method for engaging the various embodiments of bone screws to bone according to one form of the invention. As shown in FIGS. 2-5, in one embodiment, the bone within which the bone screws are engaged comprises a vertebral body V having an inner cancellous bone region 200 and an outer cortical bone region 202. As would be appreciated by those of skill in the art, the outer cortical bone region 202 of the vertebral body V is relatively harder and denser compared to the inner cancellous bone region 200.

The threaded shank 52 of the bone screw 50 is driven into engagement with the vertebral body V, with the first threaded section 70 including the helical threading 74 defining the smaller crest width $w_1$ and the greater distance $d_1$ between the upper and lower flanks of adjacent thread turns engaged within the cancellous bone region 200, and with the second threaded section 72 including the helical threading 76 defining the relatively larger crest width $w_2$ and the relatively shorter distance $d_2$ between the upper and lower flanks of adjacent thread turns engaged within the cortical bone region 202 and within cancellous bone adjacent the cortical bone region 202. As indicated above, when the bone screw 50 is driven into bone, the first threaded section 70 initially engages the bone and bone material is directed into and channeled through the volume $v_1$ between adjacent thread turns of the first helical threading 74. As the bone screw 50 is further threaded into the bone, the second threaded section 72 will engage the bone and the bone material will be directed into and channeled through the volume $v_2$ between adjacent thread turns of the second helical threading 76. Since the volume $v_2$ between adjacent turns of the second helical threading 76 is reduced compared to the volume $v_1$ between adjacent turns of the first helical threading 74, the bone material directed into the volume $v_2$ will be compressed or compacted between the upper and lower flanks of the second helical threading 76 as the second threaded section 72 is driven into the bone.

As should be appreciated, compression or compaction of bone material between the upper and lower flanks of the second helical threading 76 will tighten the bone screw 50 within the bone, thereby tending to provided more secure and stable anchoring of the bone screw 50 within the bone. While the configuration of the first helical threading 74 provides suitable bone purchase capabilities and pullout characteristics with regard to the softer cancellous bone material, the configuration of the second helical threading 76 tends to provide improved support and stability of the bone screw 50 via the compression or compaction of the cancellous bone material between adjacent turns of the second helical threading 76. The denser and more compact thread configuration of the second helical threading 76 relative to the first helical threading 74 also tends to provide more secure anchoring within the relatively harder and denser cortical region of bone. Additionally, since the first and second helical threadings 74 and 76 each have substantially equal thread pitches, threading of the second threaded section 72 into the bone will not require any additional turns relative to threading of the first threaded section 70 into the bone to fully engage the bone screw within the vertebral body V. As discussed above, following anchoring of a number of bone screws to vertebral bodies, a spinal implant such as a rod or plate may be coupled to the bone screws for treatment of the spinal column.

It should be understood that the bone screws of the present invention may be anchored within any number of vertebral bodies V, including a single vertebral body or two or more vertebral bodies. In one embodiment of the invention, the bone screws are anchored within the pedicle region of a vertebral body. However, it should be understood that the bone screws may be anchored to other portions or regions of a vertebral body. It should also be understood that the bone screws of the present invention may be anchored to a posterior, anterior, lateral, posterolateral or anterolateral aspect of the vertebral body V. It should further be understood that the bone screws of the present invention may be attached to any region of the spinal column, including the cervical, thoracic, or lumbar regions of spinal column. It should likewise be understood that the bone screws of the present invention may be attached to bone structures other than vertebral bodies, such as, for example, bones associated with the arm, leg or bones associated with other areas of the body.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A bone screw, comprising:
   A head portion; and
   a threaded shank portion having a longitudinal axis and including a single thread lead defining a thread root diameter, said single thread lead including a first helical threading extending along a first length of said threaded shank portion distal said head portion, and a second helical threading extending from a location proximately adjacent said first helical threading and along a second length of said threaded shank portion proximate said head portion, said first and second helical threadings of said single thread lead defining a substantially constant thread pitch along said first and second lengths of said threaded shank portion, said first helical threading defining a first substantially constant volume between adjacent thread turns along said first length, said second helical threading defining a second substantially constant volume between adjacent thread turns along said second length, wherein said second volume is less than said first volume, wherein said adjacent thread turns of said first helical threading define opposing thread flanks that are separated by a first distance at said thread root diameter, said adjacent thread turns of said second helical threading defining opposing thread flanks that are separated by a second distance at said thread root diameter, and wherein said second distance is less than said first distance.

2. The bone screw of claim 1, wherein said first helical threading defines a first substantially constant thread crest width along said first length, said second helical threading defining a second substantially constant thread crest width along said second length; and
wherein said first thread crest width is less than said second thread crest width.

3. The bone screw of claim 1, wherein said thread root diameter is substantially constant along said first and second lengths of said threaded shank portion, and wherein said threaded shank portion defines a substantially constant thread outer diameter along said first and second lengths of said threaded shank portion.

4. The bone screw of claim 1, wherein said first helical threading and said second helical threading each define substantially equal flank angles.

5. The bone screw of claim 1, wherein said second volume between said adjacent thread turns of said second helical threading is at least about five percent less than said first volume between said adjacent thread turns of said first helical threading.

6. The bone screw of claim 5, wherein said second volume between adjacent thread turns of said second helical threading is at least about ten percent less than said first volume between adjacent thread turns of said first helical threading.

7. The bone screw of claim 1, wherein said first length of said first helical threading and said second length of said second helical threading each extend along at least about one-quarter of an overall length of said threaded shank portion.

8. The bone screw of claim 1, wherein said first length of said first helical threading and said second length of said second helical threading each extend along at least about one-third of an overall length of said threaded shank portion.

9. The bone screw of claim 1, wherein said first length of said first helical threading and said second length of said second helical threading each extend along approximately one-half of an overall length of said threaded shank portion.

10. The bone screw of claim 1, wherein said second helical threading extends continuously from said first helical threading to define said single thread lead.

11. The bone screw of claim 1, wherein said first helical threading transitions into said second helical threading at a transition region wherein a portion of said second helical threading extends continuously from and overlaps an axially adjacent portion of said first helical threading and extends from a location adjacent a thread root diameter and gradually increases to an outer thread diameter.

12. The bone screw of claim 1, wherein said first helical threading transitions into said second helical threading at a transition region wherein a portion of said second helical threading extends continuously from and overlaps an axially adjacent portion of said first helical threading and extends from a location adjacent a thread root diameter and gradually transitions to a thread crest of said first helical threading.

13. The bone screw of claim 1, further comprising:
an elongate spinal implant sized to extend between at least two vertebrae, said elongate spinal implant coupled to said head portion of at least two of the bone screws anchored to respective ones of the vertebrae.

14. The bone screw of claim 1, wherein said first and second helical threadings of said single thread lead together define a constant and uniform outer thread diameter along said first and second lengths.

15. A bone screw, comprising:
A head portion; and
a threaded shank portion having a longitudinal axis and including a single thread lead defining a thread root diameter, said single thread lead including a first helical threading extending along a first length of said threaded shank portion distal said head portion, and a second helical threading extending from a location proximately adjacent said first helical threading and along a second length of said threaded shank portion extending up to said head portion, said first and second helical threadings of said single thread lead defining a substantially constant thread pitch along said first and second lengths of said threaded shank portion, said first helical threading defining a first substantially constant thread crest width along said first length, said second helical threading defining a second substantially constant thread crest width along said second length, wherein said first thread crest width is less than said second thread crest width, wherein adjacent thread turns of said first helical threading define opposing thread flanks that are separated by a first distance at said thread root diameter, said adjacent thread turns of said second helical threading defining opposing thread flanks that are separated by a second distance at said thread root diameter, and wherein said second distance is less than said first distance.

16. The bone screw of claim 15, wherein said thread root diameter is substantially constant along said first and second lengths of said threaded shank portion, and wherein said threaded shank portion defines a substantially constant thread outer diameter along said first and second lengths of said threaded shank portion.

17. The bone screw of claim 15, wherein said first helical threading and said second helical threading each define substantially equal flank angles.

18. The bone screw of claim 15, wherein said first length of said first helical threading extends along a distal region of said threaded shank portion and said second length of said second helical threading extends along a proximal region of said threaded shank portion; and
wherein said first helical threading defines a first substantially constant volume between said adjacent thread turns along said first length, said second helical threading defining a second substantially constant volume between said adjacent thread turns along said second length; and
wherein said second volume between said adjacent thread turns of said second helical threading is less than said first volume between said adjacent thread turns of said first helical threading to thereby compress bone material within said second volume as the bone screw is driven into bone.

19. The bone screw of claim 15, wherein said second helical threading extends continuously from said first helical threading to define said single thread lead; and wherein said first helical threading transitions into said second helical threading at a transition region wherein a portion of said second helical threading extends continuously from and overlaps an axially adjacent portion of said first helical threading and extends from a location adjacent a thread root diameter and gradually increases to an outer thread diameter.

20. A bone screw, comprising:

a threaded shank having a longitudinal axis and a single thread lead including a first helical threading extending along a first length of said threaded shank portion and a second helical threading extending from a location proximately adjacent said first helical threading and along a second length of said threaded shank portion, said first and second helical threadings of said single thread lead defining a substantially constant thread pitch along said first and second lengths of said threaded shank portion, said first helical threading defining a first volume between adjacent thread turns, said second helical threading defining a second volume between adjacent thread turns, wherein said first volume is different from said second volume, and wherein said first and second helical threadings of said single thread lead together define a constant and uniform outer thread diameter along said first and second lengths of said threaded shank; and wherein said first helical threading transitions into said second helical threading at a transition region wherein a portion of said second helical threading overlaps an axially adjacent portion of said first helical threading and extends from a location adjacent a thread root diameter and gradually increases to an outer thread diameter.

21. The bone screw of claim 20, wherein said portion of said second helical threading gradually transitions into a thread crest of said first helical threading.

22. The bone screw of claim 20, wherein said first volume between adjacent thread turns of said first helical threading is substantially constant along said first length; and wherein said second volume between adjacent thread turns of said second helical threading is substantially constant along said second length.

23. The bone screw of claim 20, wherein said first helical threading defines a first thread crest width along said first length, said second helical threading defining a second thread crest width along said second length; and wherein said first thread crest width is different from said second thread crest width.

24. The bone screw of claim 20, wherein said second helical threading extends continuously from said first helical threading.

25. The bone screw of claim 20, wherein said first length of said first helical threading extends along a distal region of said threaded shank portion and said second length of said second helical threading extends along a proximal region of said threaded shank portion; and wherein said second volume between adjacent thread turns of said second helical threading is less than said first volume between adjacent thread turns of said first helical threading to thereby compress bone material within said second volume as the bone screw is driven into bone.

26. The bone screw of claim 15, wherein said first and second helical threadings of said single thread lead together define a constant and uniform outer thread diameter along said first and second lengths.

27. The bone screw of claim 20, wherein said first and second helical threadings of said single thread lead together define a substantially constant thread pitch along said first and second lengths of said threaded shank portion.

28. The bone screw of claim 20, wherein said portion of said second helical threading and said axially adjacent portion of said first helical threading are contiguous with one another so as to define a unitary and substantially uninterrupted transition threading.

29. The bone screw of claim 20, wherein said second volume is less than said first volume; and wherein said adjacent thread turns of said first helical threading define opposing thread flanks that are separated by a first distance at said thread root diameter, said adjacent thread turns of said second helical threading defining opposing thread flanks that are separated by a second distance at said thread root diameter, and wherein said second distance is less than said first distance.

* * * * *